(12) United States Patent
Yang et al.

(10) Patent No.: US 10,456,087 B2
(45) Date of Patent: Oct. 29, 2019

(54) METHOD FOR SCORE CONFIDENCE INTERVAL ESTIMATION WHEN VITAL SIGN SAMPLING FREQUENCY IS LIMITED

(71) Applicant: KONINKLIJKE PHILIPS N.V., Eindhoven (NL)

(72) Inventors: Lin Yang, Chandler, AZ (US); Eric Thomas Carlson, New York, NY (US); Larry James Eshelman, Ossining, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/525,201

(22) PCT Filed: Nov. 16, 2015

(86) PCT No.: PCT/IB2015/058847
§ 371 (c)(1),
(2) Date: May 8, 2017

(87) PCT Pub. No.: WO2016/079654
PCT Pub. Date: May 26, 2016

(65) Prior Publication Data
US 2017/0360379 A1 Dec. 21, 2017

Related U.S. Application Data

(60) Provisional application No. 62/082,259, filed on Nov. 20, 2014.

(51) Int. Cl.
*A61B 5/00* (2006.01)
*A61B 5/0205* (2006.01)
(Continued)

(52) U.S. Cl.
CPC .......... *A61B 5/7275* (2013.01); *A61B 5/0205* (2013.01); *A61B 5/7221* (2013.01);
(Continued)

(58) Field of Classification Search
CPC ..... A61B 5/7275; A61B 5/0205; A61B 5/021; A61B 5/0022; G06F 19/00; G06F 19/3431; G16H 50/30
(Continued)

(56) References Cited

U.S. PATENT DOCUMENTS 6,251,081 B1 6/2001 Narimatsu
6,684,090 B2 * 1/2004 Ali ...................... A61B 5/1455
600/323
(Continued)

FOREIGN PATENT DOCUMENTS

WO 2014071145 A1 5/2014
WO WO-2014071145 A1 * 5/2014 ........... A61B 5/7275
WO 2014158133 A1 10/2014

*Primary Examiner* — Michael W Kahelin
*Assistant Examiner* — Sana Sahand

(57) ABSTRACT

The following relates generally to the medical monitoring arts, medical warning systems concerning a monitored patient, and so forth. In clinical settings, alarms are usually triggered when a single-parameter or a multi-parameter score exceeds certain thresholds. When a score needs to be determined, if certain parameters are not available, the common practice is to use the most recent measurements of the parameters for the score calculation. However, a patient's status may change from moment to moment. The parameters measured hours ago may not be a good indicator of the patient's current status. This uncertainty can put deteriorating patients at great risk. An embodiment uses statistical methods to estimate a range of scores and the probability of these scores if old measurements have to be used for score determination. Instead of giving a single number at a time, a confidence interval may be displayed to
(Continued)

emphasize the fact that the score is determined partially based on old measurements. If there is a chance that the actual score is higher and may exceed a critical alarm threshold, a notification can be issued to advise a new measurement reading to improve score confidence.

12 Claims, 6 Drawing Sheets

(51) Int. Cl.
    *A61B 5/021*     (2006.01)
    *A61B 5/024*     (2006.01)
    *A61B 5/08*     (2006.01)
    *A61B 5/145*     (2006.01)
    *G06F 19/00*     (2018.01)
    *G16H 40/63*     (2018.01)
    *G16H 50/30*     (2018.01)

(52) U.S. Cl.
    CPC ............... *A61B 5/021* (2013.01); *A61B 5/024* (2013.01); *A61B 5/0816* (2013.01); *A61B 5/14542* (2013.01); *G06F 19/324* (2013.01); *G16H 40/63* (2018.01); *G16H 50/30* (2018.01)

(58) Field of Classification Search
    USPC ....... 600/323, 324, 300, 364, 309, 485, 509, 600/365
    See application file for complete search history.

(56) References Cited

U.S. PATENT DOCUMENTS

| | | |
|---|---|---|
| 2006/0161091 A1 | 7/2006 | Kinouchi et al. |
| 2008/0188733 A1* | 8/2008 | Al-Ali ................. A61B 5/0205 600/364 |
| 2008/0269625 A1 | 10/2008 | Halperin et al. |
| 2009/0187082 A1* | 7/2009 | Cuddihy ............. G06F 19/3418 600/300 |
| 2010/0249549 A1* | 9/2010 | Baker, Jr. ........... A61B 5/02416 600/323 |
| 2011/0077484 A1* | 3/2011 | Van Slyke ......... A61B 5/02416 600/324 |
| 2013/0338543 A1 | 12/2013 | Gegner et al. |
| 2014/0207489 A1 | 7/2014 | Wartena et al. |
| 2014/0275818 A1* | 9/2014 | Kassem ................ A61B 5/746 600/301 |

* cited by examiner

Analytical calculation of new score

If the last EWS indicates the patient is on the edge of deterioration

Step 1: Distribution generation for individual vital signs

Step 2: Last vital signs + $\Delta t \rightarrow$ probability of passing certain threshold $p(MEWS' = 5 \mid MEWS_0 = 4)$ $= \int_i p(\text{combination } i \rightarrow MEWS\uparrow)$ $p_i = p(\Delta HR \mid HR \text{ taken } \Delta t_1 \text{ ago}) * \ldots$
$\quad * p(\Delta RR \mid RR \text{ taken } \Delta t_2 \text{ ago})$ Step 3: Indicator $\rightarrow$ probability of passing the threshold Score:

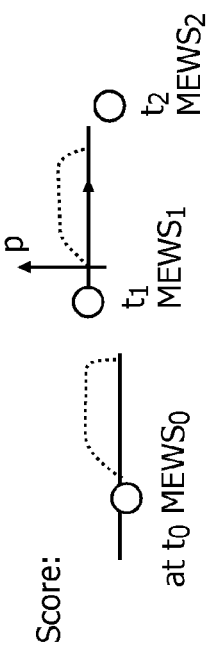

at $t_0$ MEWS$_0$   $t_1$ MEWS$_1$   $t_2$ MEWS$_2$

FIG. 3B

Alarms by individual vital sign

Step 1: Distribution generation for individual vital signs

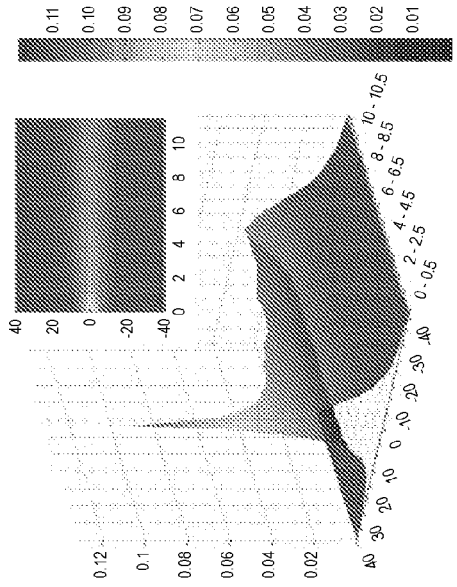

Step 2: last vital sign + $\Delta t \rightarrow$ probability of individual vital signs passing certain threshold $p(HR' > \text{threshold} \mid \text{last } HR)$

FIG. 3A

METHOD FOR SCORE CONFIDENCE INTERVAL ESTIMATION WHEN VITAL SIGN SAMPLING FREQUENCY IS LIMITED

CROSS-REFERENCE TO PRIOR APPLICATIONS

This application is the U.S. National Phase application under 35 U.S.C. § 371 of International Application No. PCT/M2015/058847, filed on Nov. 16, 2015, which claims the benefit of U.S. Provisional Application Ser. No. 62/082,259, filed Nov. 20, 2014. These applications are hereby incorporated by reference herein, for all purposes.

BACKGROUND

The following relates generally to the medical monitoring arts, medical warning systems concerning a monitored patient, and so forth.

Hospitals, nursing homes, and other medical facilities commonly use an early warning scoring (EWS) system designed to provide predictive information as to whether a given patient is likely to require emergency care, such as being admitted to an intensive care unit (ICU) or cardiac care unit (CCU). By way of illustration, one known EWS system known as the Modified Early Warning System (MEWS) computes a score based on physiological parameters including: blood pressure; heart rate; respiration rate; patient temperature; and level of consciousness (for example, quantified using the AVPU scale). In MEWS, each of these physiological parameters has a normal range with score zero, and the score component for the physiological parameter increases as the value moves further out of the normal range. By way of illustration, a heart rate in the normal range of 51-100 beats per minute (BPM) scores zero, while a rate of between 41-50 or 101-110 BMP scores 1, a rate of less than 40 or between 111-129 BPM scores 2, and a rate of greater than 130 BPM scores 3. The AVPU scores 0 for "alert," 1 for "voice response," 2 for "pain response," and 3 for "unresponsive." The scores for the physiological parameters are totaled, and a score greater than a threshold, e.g. 5, is considered an action trigger (for example, triggering an emergency medical team call, triggering transfer to ICU or CCU, et cetera).

Conventionally, EWS systems have been paper-based systems. For example, the nurse suitably fills in parameter scores on a printed table, and adds the values together to produce the EWS score.

BRIEF SUMMARY

In accordance with one aspect, a patient monitoring system including a display device; and an electronic data processing component programmed to perform a patient monitoring method including, at each successive current time: determining a patient status value at the current time based a most recently received measurement for each of one or more input physiological parameters; estimating a confidence interval for the patient status value at the current time based on a time interval between the current time and a receipt time of the most recently received measurement for each of the one or more input physiological parameters; and displaying patient status information on the display device wherein the displayed patient status information is based on both the patient status value at the current time and the estimated confidence interval for the patient status value at the current time. The patient status value may be an early warning system (EWS) score and the determining may comprise computing the EWS score based on the most recently received measurements of a plurality of input physiological parameters. In some embodiments the EWS score assumes only integer values.

In accordance with another aspect, in a patient monitoring system as set forth in the immediately preceding paragraph, the patient status value at the current time together with the estimated confidence interval for the patient status value at the current time may be displayed on the display device. In embodiments in which the one or more input physiological parameters include a plurality of input physiological parameters, the estimating may comprise: estimating a confidence interval at the current time for each input physiological parameter based on the time interval between the current time and the receipt time of the most recently received measurement for the input physiological parameter; and estimating the confidence interval for the patient status value at the current time based on the estimated confidence intervals at the current time for the plurality of input physiological parameters. In some embodiments, the confidence interval is estimated based on a statistical distribution of measurements for the input physiological parameter(s) stored in a past patients database. In accordance with another aspect, a most stale parameter may be determined as the parameter of the plurality of parameters that most contributes to the confidence interval for the patient status value. The most stale parameter may be displayed on the display, for example in the form of a recommendation to update (that is, remeasure) the most stale parameter.

In accordance with another aspect, a patient monitoring system includes a display device, and an electronic data processing component programmed to perform a patient monitoring method including: receiving measurements of physiological parameters; and at each successive current time: (i) computing an early warning system (EWS) score based on the most recently received measurements of physiological parameters, (ii) estimating a confidence interval for the EWS score based on time intervals between the current time and receipt times of the most recently received measurements of physiological parameters, and (iii) displaying EWS information on the display device (10) wherein the displayed EWS information is based on both the computed EWS score and the estimated confidence interval for the EWS score. The displayed EWS information may include the computed EWS score and the estimated confidence interval for the EWS score.

In accordance with another aspect, a method comprises: determining a patient status value at a current time based a most recently received measurement for each of one or more input physiological parameters; estimating a confidence interval for the patient status value at the current time based on a time interval between the current time and a receipt time of the most recently received measurement for each of the one or more input physiological parameters; and displaying patient status information on a display device. The displayed patient status information is based on both the patient status value at the current time and the estimated confidence interval for the patient status value at the current time.

One advantage resides in improving effectiveness and accuracy of a patient monitor in conveying a patient's risk.

Another advantage resides in better allocation of hospital resources. For example, resources may be allocated to patients who are more at risk.

Another advantage resides in providing a patient monitor capable of recommending physiological parameter measurements, such as in order to facilitate patient risk assessment.

Still further advantages of the present invention will be appreciated to those of ordinary skill in the art upon reading and understand the following detailed description. It is to be appreciated that none, one, two, or more of these advantages may be achieved by a particular embodiment.

The invention may take form in various components and arrangements of components, and in various steps and arrangements of steps. The drawings are only for purposes of illustrating the preferred embodiments and are not to be construed as limiting the invention.

FIG. 1 diagrammatically shows an embodiment of a patient monitoring system.

FIG. 3A shows an example of a single-parameter alarm system.

FIG. 3B shows an example of an analytical calculation of a new score in a multi-parameter discrete scoring system.

Figure 5:
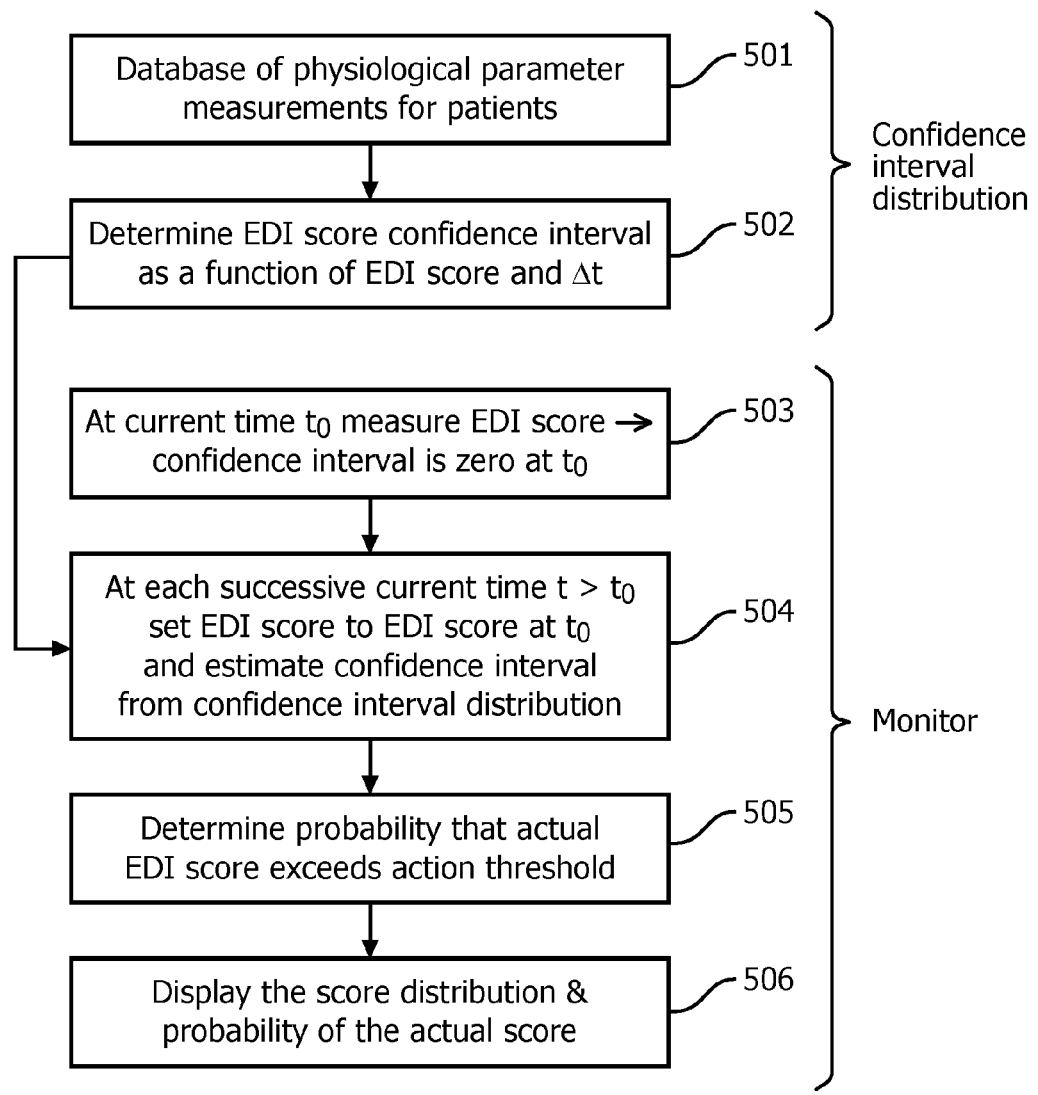

FIG. 5 diagrammatically shows a process related to the probability of a score exceeding a threshold.

Figure 6:
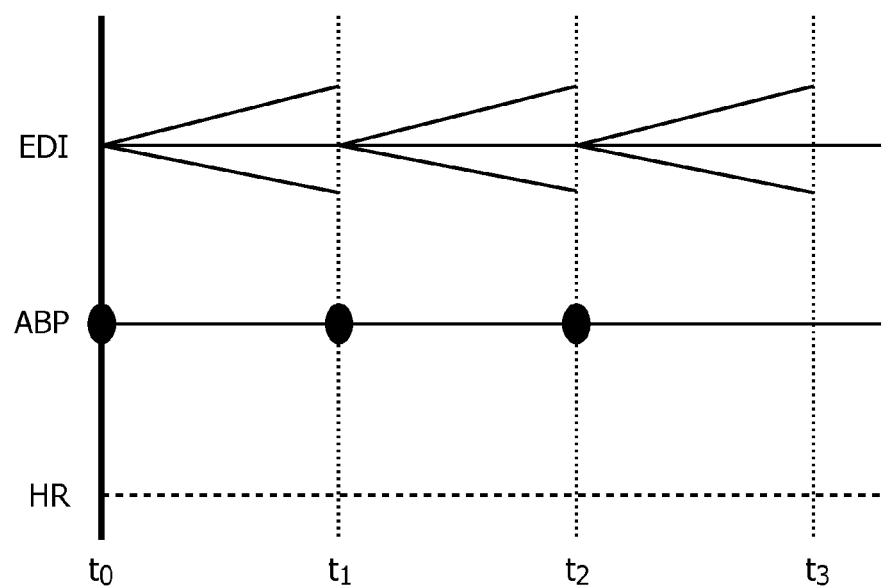

FIG. 6 shows an example where an EDI is calculated based on heart rate (HR) and ambulatory blood pressure (ABP).

Figure 7:
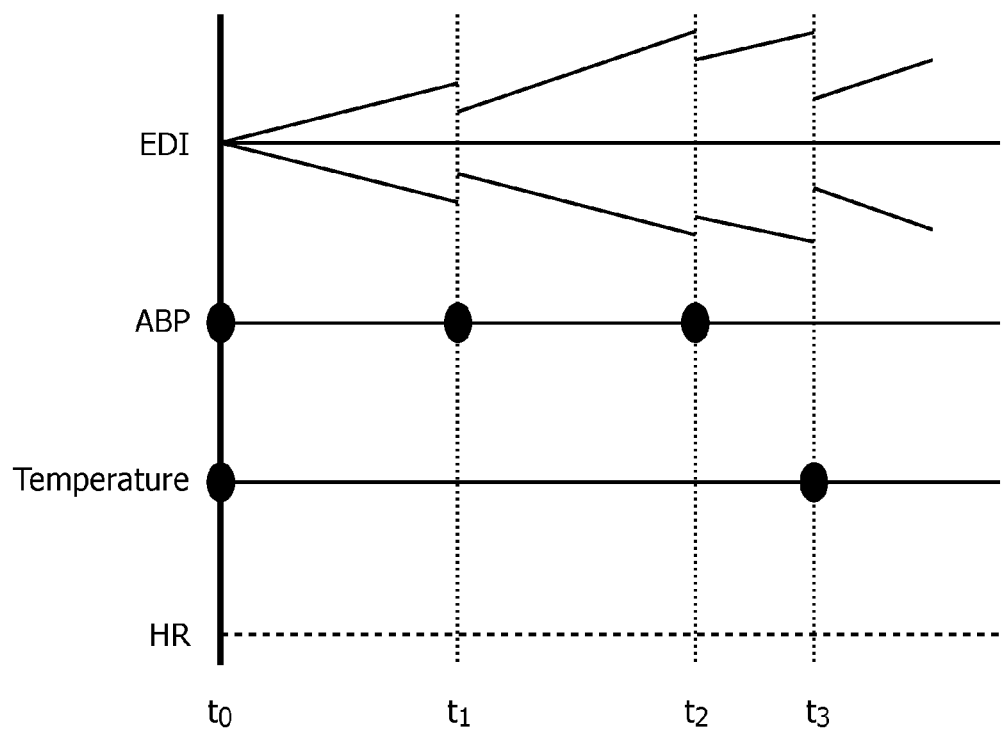

FIG. 7 shows an example where an EDI is calculated based on HR, temperature and ABP.

DETAILED DESCRIPTION

Patients are commonly monitored by an electronic patient monitor that receives multiple physiological parameter inputs, such as heart rate (HR), blood pressure, and/or respiration rate (RR), and plots trends and/or displays instantaneous values for each parameter. It may be advantageous for such a patient monitor to also compute and display an Early Warning System (EWS) score that provides an indication of whether patient condition may be degrading sufficiently to call for remedial action. The EWS score can be computed based on monitored values acquired by the patient monitor, possibly along with values of other parameters entered by the nurse or read from the Electronic Medical Record (EMR). To illustrate using the previous MEWS example, the patient monitor may continuously monitor the heart rate, blood pressure, and respiration rate (possibly along with other parameters such as SpO$_2$). (The term "continuous" or "real time" monitoring as used herein indicates acquiring samples fast enough to approximate continuous, real time data, e.g. measuring a heart rate sample every few seconds). On the other hand, patient temperature may be acquired by the nurse on an occasional basis, and patient alertness may be checked even more infrequently. These relatively infrequent physiological parameter measurements may be delivered to the patient monitor via manual entry into the monitor, or by reading the EMR over a hospital data network. The EWS score can be displayed on the patient monitor as another monitored physiological parameter (albeit synthesized), for example as a real-time numeric value and/or as a trend line. This has advantages including placing the EWS score on the same display device as other physiological parameters that are frequently reviewed by the nurse, and automatically updating the EWS score as successive measurements (e.g. heart rate) are received (by automatic measurement of the physiological sensor, input to the monitor by the nurse, data read over the hospital data network, or so forth).

However, a difficulty recognized herein is that such a display can be misleading because medical personnel may misunderstand the displayed EWS score as being an accurate real-time value. In practice, however, the "ground truth" EWS score can change from moment to moment as the patient condition improves or worsens, while the EWS score displayed on the patient monitor only reflects the last measurement of each input physiological parameter. For example, if patient temperature is measured hourly, then the displayed EWS score may be up to one hour out of date due to reliance on an "old" temperature measurement. Similarly, if alertness is only measured twice per day, then the displayed EWS score may be based on an alertness score that is up to 12 hours old. If different physiological parameters are measured at different times, the displayed EWS score may never be completely current.

Thus, a problem exists in that the patient monitor provides an EWS score that appears to be a real-time value, but which in fact may be out of date due to various changes in the patient that have occurred since the last patient measurement(s). A further problem exists in that, even if medical personnel recognize the EWS score may be out of date, it is not readily apparent how to improve the EWS score accuracy.

These problems can have various impacts:

First, uncertainty in score determination: Using old measurements for the calculation of a current score assumes a patient's status remains unchanged between two measurements. This is usually not the case. Scores determined using old measurements may not be an accurate deterioration indicator considering how dynamic a patient's condition can be.

Second, false negatives can occur, in which the (outdated) EWS score indicates the patient is stable when in actuality the patient's condition has deteriorated to a point at which action may be called for. A patient's condition is dynamic over time. However, displaying such a "false negative" score may give clinicians false impression that the patient's condition is stable.

Third, imbalanced resource allocation: Excessive resources may go to patients whose score is only slightly higher than a stability/instability threshold. Even after the patient has been stabilized, the EWS score will remain the same until the next measurements are taken which reflect the patient's stabilization. This means that the EWS score may fail to quickly reflect efficacy of the remedial action.

Still further, outdated EWS scores can lead to distrust of the physiological measurements and/or EWS system: Scores and measurements are presented as being accurate current values, regardless of the staleness of the physiological measurements. Scores become decreasingly reliable with time, and so scores using older data are more prone to false positives and false negatives. But because this is not communicated to caregivers, experience with such scores negatively impacts user sentiment of the system as a whole, and even scores with new data are treated as suspect.

One way to address these problems is by increasing the frequency of vital sign monitoring, most efficiently through bed-side monitors, but this increases patient care costs and depletes caregiver resources. Moreover, some input measurements such as alertness cannot practically be performed on a frequent basis. (The patient is disturbed each time nurse/patient interaction is used to assess alertness).

Disclosed herein are improved patient monitoring systems and methods that provide medical personnel with more realistic indication of physiological parameters and/or EWS scores by statistically assessing and displaying uncertainty of these values. In some embodiments, medical personnel may also be informed of which parameter(s) are advantageously updated (e.g. remeasured) in order to efficiently reduce the uncertainty. This technology is suitably offered as part of a patient monitoring system.

Some disclosed embodiments use statistical methods to estimate a range of scores and the probability of these scores if old measurements have to be used for score determination. Instead of presenting the score as a single value, one aspect displays the score together with a confidence interval to emphasize the fact that the score is determined based on old measurements.

One embodiment includes the following operations: (1) generate statistical distribution of parameters/scores by retrospectively analyzing past patient data, (2) at a given time from last measurement, estimate the confidence interval for the actual score, and (3) display probable scores or alarms with their probability values. With this approach, a range of scores can describe a patient's current status more accurately even though only old measurements are available.

The term "confidence interval" in statistics generally refers to a statistical estimation of a range within which a parameter falls within a population. For example, a 95% confidence interval for a parameter indicates that, for a population of statistically significant size, 95% of the members of the population will exhibit a value for the parameter falling within the 95% confidence interval. As used herein, the term "confidence interval" is intended to encompass uncertainty metrics that are explicitly expressed as confidence intervals, as well as uncertainty metrics expressed using other formalisms such as margin of error (for example, a confidence interval may be expressed as a margin of error, e.g. the parameter is known with a ±5% margin of error).

Figure 1:
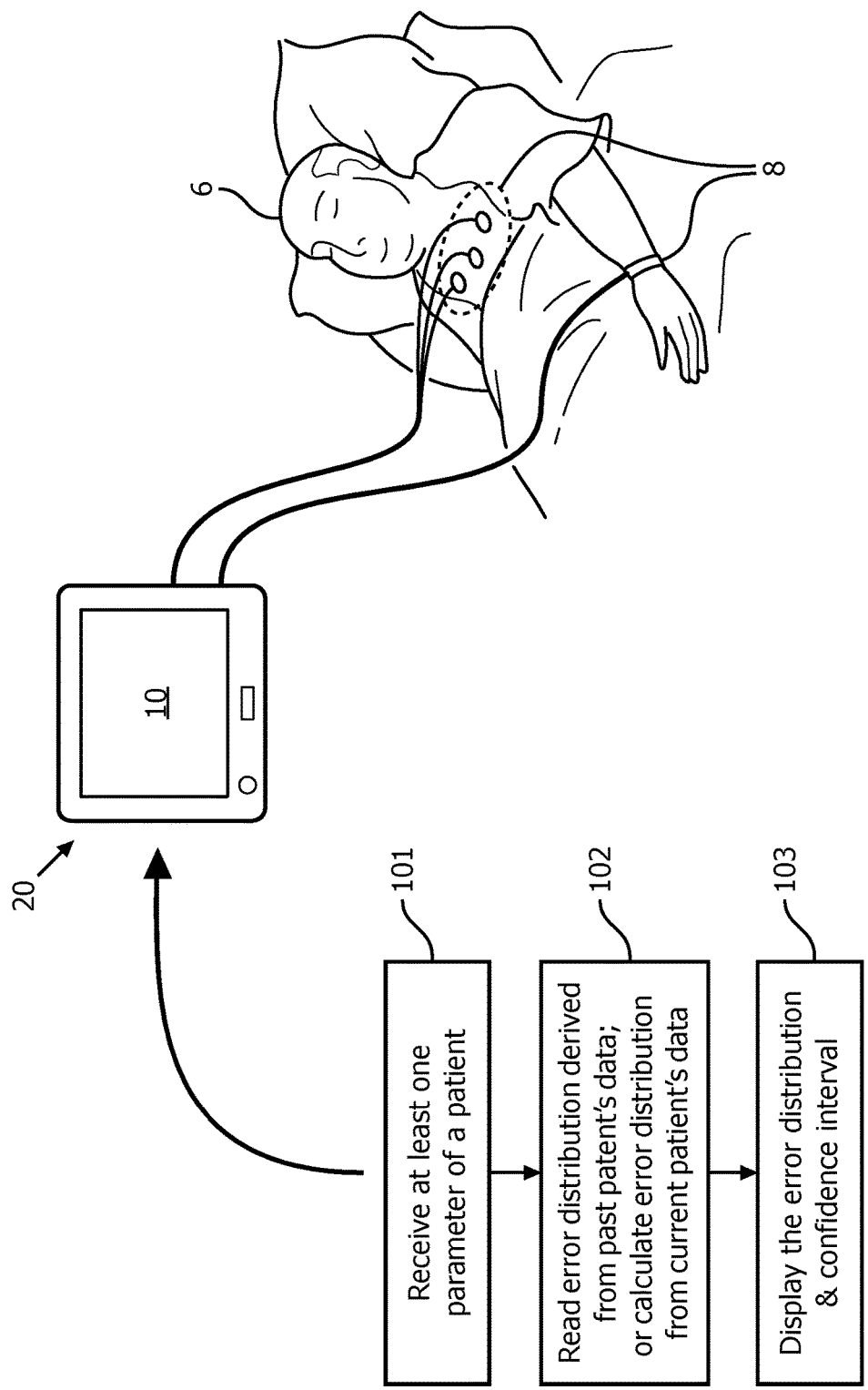

With reference to FIG. 1, a patient 6 is monitored by a plurality of physiological sensors 8, such as by way of illustrative example, one or more of the following: a pulse sensor such as electrocardiograph (ECG) electrodes of an ECG that provides pulse and ECG traces, an $SpO_2$ sensor (providing pulse and peripheral oxygen), a blood pressure sensor, a respiration sensor, or so forth. A patient monitor 20 includes a display device 10 and an electronic data processing component (not shown) such as an electronic microprocessor, microcontroller, or so forth executing instructions stored on a non-transitory storage medium (e.g. a hard drive, read-only memory i.e. ROM, flash memory, or so forth). In some embodiments the patient monitor 20 may be embodied as a computer with a peripheral card providing inputs for the sensors 8. In other embodiments the patient monitor 20 may be a dedicated electronic patient monitor device with such inputs. The patient monitor 20 reads or receives physiological measurements from the physiological sensors 8. Some sensors may include on-board electronics that generate the physiological measurement as a digital value that is transmitted to the patient monitor 20. Some sensors may provide an analog signal such a voltage or current that is converted to a digital value by an analog-to-digital (A/D) converter of the patient monitor 20. Some sensors may directly measure the physiological parameter of interest, while other sensors may measure physiological data that are then processed by the patient monitor 20 to generate the physiological measurement of interest. By way of an illustrative example, in the case of an ECG the directly measured physiological data may be ECG electrode voltages, and the patient monitor 20 then processes these data by computing lead voltages (differential voltages between selected electrodes) and/or by computing a heart rate based on signal periodicity. The patient monitor 20 may display the ECG lead traces as monitored physiological parameters, and/or may display the heart rate as a trend and/or as a current numeric value. The illustrative sensors 8 are in wired connection with the patient monitor 20, but sensors may additionally or alternatively be connected wirelessly, e.g. by a Bluetooth or Zigbee protocol wireless link, an infrared link, or so forth. The various physiological parameters obtained from the physiological sensors 8 are suitably displayed on the display device 10 as traces (that is, values plotted as a function of time) and/or as current numerical values. The patient monitor 20 may be variously configurable, for example enabling user selection of which parameters to display, the display format (numeric value, trace, or both), setting upper and/or lower alarm limits for various parameters, or so forth. In some embodiments, the patient monitor 20 further includes one or more user input devices such as a keyboard (possibly implemented as an LCD keyboard or a touch-sensitive area of the display), via which a nurse may enter values for one or more parameters that are not measured by the sensors 8 but rather measured by the nurse (for example, an alertness score, a manually acquired patient temperature reading, et cetera). In some embodiments the patient monitor 20 is connected with an electronic data network (e.g. a hospital network and/or the Internet), and in such embodiments the patient monitor 20 may receive measurements for one or more patient physiological parameters over the network (for example, hematology laboratory results).

The patient monitor 20 or other computational device also computes confidence intervals for one or more physiological parameters, and/or for an EWS score or other derived parameter (generally, a patient status value), and displays patient status information on the display device 10 that is based on both the patient status value at the current time and the estimated confidence interval for the patient status value at the current time. The patient monitor 20 or other computational device may, for example: receive at least one parameter of a patient (step 101), read an error distribution derived offline from past patent's data (or in an alternative approach calculate an error distribution online from current patient's data) (step 102), and display the error distribution and confidence interval (step 103).

In the following, two illustrative embodiments are described that are suited for EWS score estimation using different EWS scoring systems. The first is most suitable in clinical settings where single-parameter alarms or discrete scoring models are used. The second is most suitable in clinical settings where continuous scoring models are used. A further illustrative embodiment combines elements of the foregoing embodiments.

The first illustrative embodiment pertains to score estimation for single-parameter alarms or discrete scoring models. Generation of the distribution for individual parameters can be performed as follows, where it is assumed that at time $t_0$, a vital sign is measured and the value is $v_0$. (The terms "physiological parameter" and "vital sign" are used interchangeably herein.) At a later time t', no new measurement is available, but the actual value of the parameter at this moment is denoted herein as v', so that the error caused by using the old measurement is $\Delta v = v' - v_0$. The actual values of v' and $\Delta v$ is not known, but the probability of v' and $\Delta v$ can be estimated by retrospectively analyzing past patient data as follows.

If a patient has N measurements $v_1, v_2, \ldots v_N$ taken at $t_1, t_2, \ldots, t_N$. For each this provides a set $\{\Delta v_j = v_j - v_i, \Delta t_j = t_j - t_i,$ where $t_j > t_i\}$. Aggregating the $\Delta v$ and $\Delta t$ of the same vital sign from all the patients, an error distribution can be estimated. Here by "error" we mean the uncertainty of the value when an old measurement is used.

Figure 2:
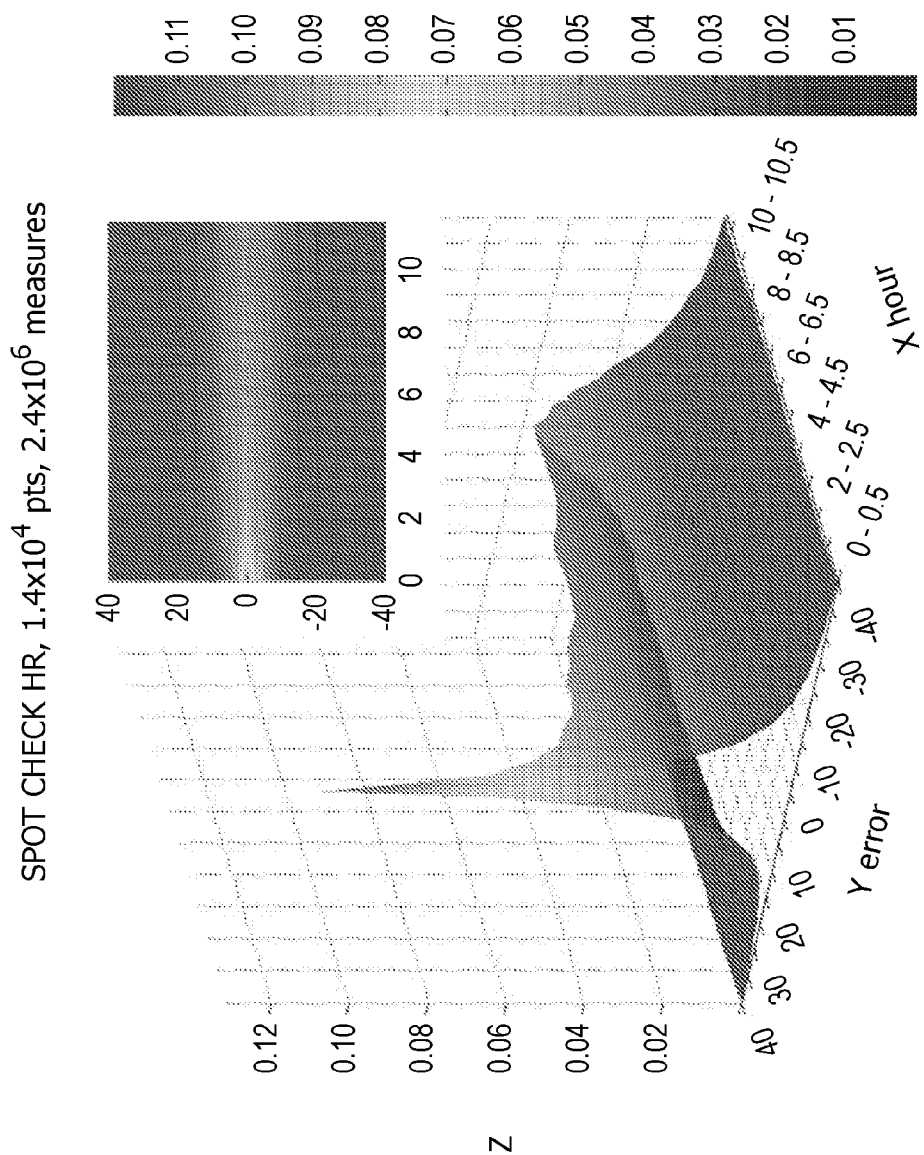
FIG. 2 shows an error distribution for a heart rate.

With reference to FIG. 2, an example of the error distribution of heart rate is plotted. The x axis is the time delay $\Delta t$, the y axis is the error $\Delta v$, and the z axis is the probability of error. It is seen that using measurements taken hours ago causes significant uncertainty. In general, the magnitude of error increases as the time $\Delta t$ since the last measurement increases.

Score or alarm confidence interval estimation can be performed as follows. In general, an alarm can be triggered by a single-parameter or a multi-parameter score exceeding a certain threshold or thresholds.

In a single parameter case, assume at to, a parameter, e.g., HR, is measured to be $v_0$. The probability of a single-parameter alarm based on HR exceeding a threshold at a later time t' is:

$p(HR'>threshold|most\ recent\ measure\ taken\ \Delta t\ ago)$ where the probability can be obtained from the error distribution as described above. For example, the probability could be obtained from the error distribution shown in FIG. 2.

In a multi-parameter case, the probability of a multi-parameter score exceeding a certain threshold can be analytically calculated. Taking the Modified Early Warning System (MEWS) as an illustrative example, a situation is deemed to call for immediate attention when the MEWS score indicates the patient is on the edge of deterioration. For example, a score 5 is taken as the critical threshold in some MEWS implementations. The MEWS score at time $t_0$ is denoted here as $MEWS_0$. Consider an illustrative example in which $MEWS_0=4$. If, as time progresses forward from to, the probability of the actual score being 5 becomes high due to the confidence interval increasing with time since the last measurement, a notification can be issued to advise a new measurement reading to improve score confidence.

The probability of the actual score being 5 can, for example, be analytically calculated by:

$p(MEWS'=5|MEWS_0=4)=\int_i p(combination\ i \rightarrow MEWS \uparrow)$ where the probability of each combination is:

$p_i=p(\Delta HR|most\ recent\ HR\ taken\ \Delta t_1 ago)^* \ldots * p(\Delta RR|most\ recent\ RR\ taken\ \Delta t_2\ ago)$ Various combinations of parameters can increase the value of MEWS to 5. Examples include: HR scores one more point while other parameters remain the same; HR and others remain the same while RR scores one more point; or HR scores two more points while RR decreases for one, etc. But, as the MEWS is a discrete scoring system, the number of combinations is limited and the probability of actual score greater than 5 can be analytically calculated.

In general, as time progresses forward from the time $t_0$ of last measurement, the uncertainty (confidence interval) of the EWS score increases. The confidence interval as a function of time since $t_0$ is, in some embodiments, suitably characterized by statistical analysis of patient data in a past patients database as described for example with reference to FIG. 2. Additionally or alternatively, the confidence interval may be estimated based on past data for the current patient 6 undergoing current monitoring. For example, the statistical analysis described with reference to FIG. 2 can be applied to past acquired data for the current patient 6. This approach accounts for historical variability of parameters for the current patient 6. For example, if the HR for the current patient 6 has been steady at about 70 bpm in the past and has not gone above 80 bmp or below 65 bpm, then the interval [65,80] bpm may be a reasonable confidence interval for the HR.

If the confidence interval for the EWS score as time progresses past to increases to a point at which there is a significant likelihood that the actual EWS score exceeds the threshold for action, various remedial actions can be taken. In one possible remediation, a warning is displayed on the display device 10 indicating that the EWS score is not currently reliable. This can be useful to medical personnel so that they do not place undue reliance upon the current EWS score; however, it does not inform medical personnel as to how the EWS score might be made reliable again. In some embodiments, remediation additionally or alternatively includes informing medical personnel of which physiological parameter measurement is most stale. As used herein, the most stale parameter is the parameter that most contributes to the uncertainty of the EWS score. To this end, the patient monitor 20 can display a message on the display device 10 indicating the stale parameter and recommending obtaining a new measurement of the stale parameter. In general, instead of, or in addition to, displaying scores calculated based on the most recent measurements taken at to, the confidence interval, the probability of the actual score exceeding higher decision-making thresholds, or other information based on the calculated confidence interval can be displayed. Recommendations can be provided, such as additional spot check to confirm if the actual score is in a dangerous zone.

FIG. 3 further illustrates various aspects. In a single-parameter alarm system (FIG. 3A), the first step is to estimate the error distribution caused by using old measurements. This corresponds to FIG. 2. The second step is to calculate the confidence interval for the vital sign at time $t>t_0$ and the probability that the vital sign exceeds a certain threshold for $t>t_0$. (For example, the "certain threshold" may be a threshold for taking some remedial action such as administering a medication or calling the on-call physician.) The confidence interval can be displayed with the score and notifications can be sent when the probability of exceeding the certain threshold is high.

In a multi-parameter discrete scoring system (FIG. 3B), the first step is to estimate the error distribution of each physiological parameter. The second step is to calculate the probability of the actual score exceeding the next decision-making threshold (e.g., actual MEWS equals 5 while the score calculated from the most recent measurement is 4). The last step is to display the probability with the score. FIG. 3B shows a diagrammatic example of the display. The solid lines extending horizontally from $t_0$ and $t_1$ are the MEWS score calculated based on the most recent measurements. All parameters used to compute the MEWS score are measured at time $t_0$, and again at time $t_1$, and again at time $t_2$. Thus, the MEWS scores at times $t_0$, $t_1$, and $t_2$ are considered exact (within the measurement accuracy), and the confidence interval is zero at times $t_0$, $t_1$, and $t_2$. In the time interval between $t_0$ and $t_1$, the dotted line extending from to plots the probability of the actual score exceeding the decision-making threshold. The probability increases with time until new measurements are available at $t_1$.

In the previous embodiments, the patient status information that is displayed along with estimated confidence interval information comprises MEWS scores, which is a discrete valued quantity as it only assumes integer values. As another illustrative example, the early deterioration indicator (EDI) is considered. This is a continuous valued parameter, rather than a discrete valued parameter as in MEWS. For a continuous valued parameter such as EDI, the analytical calculation described previously may still be used but is computationally intensive. But, the confidence interval of scores can be estimated by a method similar to the above mentioned single-parameter alarm scenario. The following description assumes that at $t_0$, all physiological parameters upon which EDI is based are newly measured and an EDI score $s_0$ is calculated, for which the confidence interval is zero (that is, the EDI score $s_0$ at time $t_0$ has zero uncertainty, as measurement error is being neglected here). At a later time $t'>t_0$, when no new score is available, the score $s_0$ continues to be plotted or displayed for $t'>t_0$. If the actual (unknown) score at this moment $t'$ is $s'$, then the error caused by using the old value is $\Delta s = s' - s_0$. Again, the actual values of $s'$ and $\Delta s$ are not known. But the probability of $s'$ and $\Delta s$ can be estimated by retrospectively analyzing past patient data (typically for patients other than the current patient 6, although past data from the current patient 6 may also be included), similarly to as was described with reference to FIG. 2. If a patient has N scores $s_1, s_2, \ldots s_N$ taken at $t_1, t_2, \ldots t_N$ respectively, then for each $s_j$, we obtain a set $\{\Delta s'_j = s_j - s_i, \Delta t_j = t_j - t_i, \text{ where } t_j > t_i\}$. Aggregating the $s'$ and $\Delta t$ from all the patients, an actual score distribution can be estimated.

Figure 4:
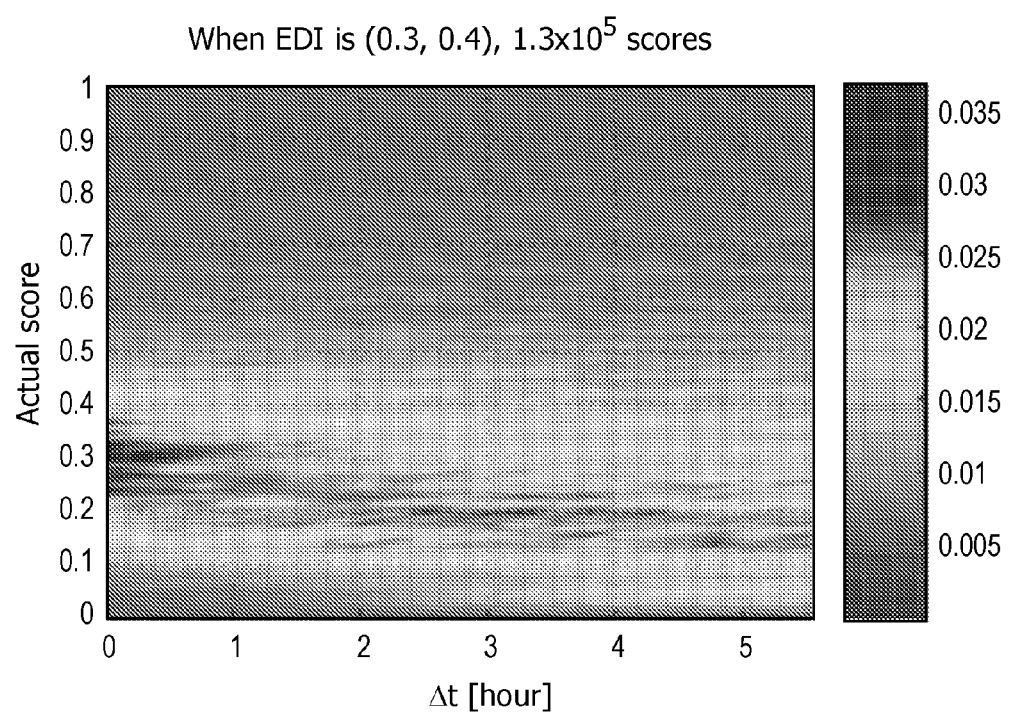
FIG. 4 shows a score distribution of early deterioration indicator (EDI) when the most recent score is in a particular range.

With reference to FIG. 4, an example is shown of the score distribution of EDI when the most recent score is in the range of 0.3~0.4. The x axis is the time delay $\Delta t$, the y axis is the actual score $s'$, and the color indicates the probability of the actual score. The uncertainty of the EDI score at a given time t separated by a delay $\Delta t$ from the time $t_0$ of the last set of measurements can be estimated from this calibration data.

The EDI score confidence interval estimation can then be performed as follows. Assume the score at $t_0$ is $s_0$. The probability of the actual score at a later time $t'$ is:

$p(\text{EDI'}|\text{most recent EDI taken } \Delta t \text{ ago})$ where the probability p can be obtained, for example, from step 1 of either FIG. 3A or 3B.

With reference now to FIG. 5, an illustrative more specific example of a process suitably performed by the patient monitor 20 is described. The process includes two phases: (1) a confidence interval distribution generation phase (steps 501, 502); and (2) a patient monitoring phase (steps 503, 504, 505, 506) during which the current patient 6 is monitored. In the step 501, a database of physiological parameters for past patients is provided. This may comprise a log of measurements stored in memory of the patient monitor 20, and/or may comprise logs of measurements accrued from a plurality of patient monitors, for example used throughout the Intensive Care Unit or other medical facility. In the step 502, the physiological measurements from the database are used to generate or estimate the distribution of actual score as a function of (i) the most recently generated score and (ii) the time interval $\Delta t$ since last set of measurements used to generate that most recent score. Thus, the confidence interval distribution is generated.

Thereafter, the monitoring phase is performed, in which the current patient 6 is monitored. In step 503, the EDI is measured and the confidence interval is set to zero (or to some small value indicative of the measurement uncertainty). At each successive current time, the EDI score remains set to the EDI score measured at $t_0$, but a confidence interval is estimated from the confidence interval distribution (e.g. step 504 of FIG. 5) using the EDI score at $t_0$ and the time interval since to as inputs. In some embodiments a probability is determined that the actual EDI score exceeds an action threshold (e.g. step 505 of FIG. 5). The EDI score of step 503, 504 is displayed for $t_0$ and each successive time (step 506 of FIG. 5), along with the confidence interval and optionally also the probability that the action threshold is exceeded. Additionally or alternatively, if the probability that the current EDI score exceeds the action threshold is sufficiently high, a notification may be sent that informs a user to update one or more of the measured parameters in order to obtain a more accurate EDI score. That is, a notification can be issued to advise a new measurement reading to improve EDI score confidence.

FIG. 6 shows a diagrammatic example of the display where the uncertainty range (i.e. confidence interval) of the EDI score is calculated based only on HR and ABP. The dotted line corresponding to HR demonstrates that HR is measured frequently enough to approximate continuous measurement, and so HR does not contribute to the uncertainty of the EDI. On the other hand, ABP is measured only at $t_0$, $t_1$ and $t_2$. Thus, in FIG. 6, the EDI score is exactly known only at the point when all of the parameters are known (e.g. at $t_0$, $t_1$, and $t_2$ the confidence interval is zero). As time elapses since the last measurement, the EDI score uncertainty increases and range of EDI may be estimated by retrospectively analyzing past patient data, as discussed above. Also as time elapses, the EDI range in generally, but not always, increases. It should be noted that although FIG. 6 diagrammatically shows linear symmetrical increases above/below the EDI score at $t_0$, this does not have to be the case. The changes do not have to be linear, or symmetrical in the plus/minus directions.

FIG. 7 shows another diagrammatic example of the display. Here, the EDI uncertainty range is calculated based on ABP, HR and temperature. Similar to FIG. 6, the dotted line corresponding to HR illustrates that HR is measured frequently enough to approximate a continuous measurement. On the other hand, temperature is measured only at times $t_0$ and $t_3$, and ABP is measured only at times $t_0$, $t_1$ and $t_2$. It is noted that these times do not coincide in this example—that is, the ABP and temperature are not measured at the same time, but rather at different times. Thus, except at $t_0$, there is no point in time at which all physiological parameters contributing to the EDI score are simultaneously measured. As in the previous cases, as time elapses since the last measurement of a given physiological parameter, the range of EDI may be estimated by retrospectively analyzing past patient data, as discussed above. Because, in the example of FIG. 7, the parameters are only all known at to, the confidence interval is only zero at $t_0$—the confidence interval is not zero at $t_1$, $t_2$, and $t_3$. FIG. 7 demonstrates that, in a multi-parameter system, measuring one physiological parameter contributing to the EWS score at a given time may not be enough to make the score known with absolute certainty, since other parameters contributing to the EWS score may be "old" and hence uncertain. But, the measurement of a parameter contributing to the uncertainty does reduce the uncertainty, as seen by the abrupt reduction in confidence interval after each measurement (that is, at $t_1$, $t_2$, $t_3$). That is, the measurement does still lead to knowing the (illustrative) EDI score with more certainty. For example, at $t_1$, when ABP is measured, the confidence interval of the EDI score reduces, but the EDI is still not known with absolute certainty because of the elapsed time since the temperature was measured. It is again noted that although FIG. 7 shows linear symmetrical confidence interval increases about the last EDI score, this does not necessarily have to be the case. The changes do not have to be linear, or symmetrical in the plus/minus direction.

It will be further appreciated that the patient monitoring techniques disclosed herein may be embodied by a non-transitory storage medium storing instructions readable and executable by an electronic data processing device (e.g. the patient monitor 20) to perform the disclosed techniques. Such a non-transitory storage medium may, for example, comprise a hard drive or other magnetic storage medium, an optical disk or other optical storage medium, a cloud-based storage medium such as a RAID disk array, flash memory or other non-volatile electronic storage medium, or so forth.

Of course, modifications and alterations will occur to others upon reading and understanding the preceding description. It is intended that the invention be construed as including all such modifications and alterations insofar as they come within the scope of the appended claims or the equivalents thereof.

The invention claimed is:

1. A patient monitoring system comprising:
   a display device; and
   an electronic data processing component programmed to perform a patient monitoring method including, at each successive current time:
      determining a patient status value at the current time based on a most recently received measurement for each of a plurality of input physiological parameters, wherein the most recently received measurements for at least one of the plurality of input physiological parameters is not a continuous measurement, and wherein one or more of the plurality of input physiological parameters are measured via one or more sensors attached to the patient;
      determining a plurality of time intervals, wherein each time interval is between the current time and a receipt time of the most recently received measurement for a respective one of the plurality of input physiological parameters;
      estimating a confidence interval for the patient status value at the current time by applying the patient status value and the plurality of time intervals to a confidence interval distribution; and
      displaying patient status information on the display device wherein the displayed patient status information is based on both the patient status value at the current time and the estimated confidence interval for the patient status value at the current time.

2. The patient monitoring system of claim 1, wherein the patient status value is an early warning system (EWS) score and determining the patient status value comprises computing the EWS score based on the most recently received measurements of the plurality of input physiological parameters.

3. The patient monitoring system of claim 1, wherein displaying patient status information comprises displaying on the display device the patient status value at the current time together with the estimated confidence interval for the patient status value at the current time.

4. The patient monitoring system of claim 1, wherein estimating the confidence interval at the current time for each input physiological parameter comprises:
   estimating the confidence interval based on a statistical distribution of measurements for the input physiological parameter stored in a past patients database.

5. The patient monitoring system of claim 1, wherein estimating the confidence interval at the current time for each input physiological parameter comprises:
   estimating the confidence interval based on data collected from the patient.

6. The patient monitoring system of any claim 1, further comprising: determining a most stale parameter as the parameter of the plurality of parameters whose confidence interval contributes most to the estimated confidence interval for the patient status value; and
   displaying on the display device an indication of the most stale parameter.

7. The patient monitoring system of claim 1, further comprising:
   estimating a probability that the patient status value exceeds a threshold based on the determined patient status value at the current time and the estimated confidence interval for the patient status value at the current time;
   wherein the displaying of patient status information on the display device includes displaying an indication of the probability that the patient status value exceeds the threshold.

8. A method comprising:
   determining a patient status value at a current time based on a most recently received measurement for a plurality of input physiological parameters, wherein the most recently received measurement for at least one of the plurality of input physiological parameters is not a continuous measurement, and wherein one or more of the plurality of input physiological parameters are measured via one or more sensors attached to the patient;
   determining a plurality of time intervals, wherein each time interval is between the current time and a receipt time of the most recently received measurement for a respective one of the plurality of input physiological parameters;
   estimating a confidence interval for the patient status value at the current time by applying the patient status value and the plurality of time intervals to a confidence interval distribution; and
   displaying patient status information on a display device, wherein the displayed patient status information is based on both the patient status value at the current time and the estimated confidence interval for the patient status value at the current time.

9. The method of claim 8, wherein the patient monitoring method further includes:
   determining a most stale parameter as the parameter of the plurality of parameters whose confidence interval contributes most to the estimated confidence interval for the patient status value; and
   displaying on the display device an indication of the most stale parameter.

10. The method of claim 8, wherein the confidence interval includes (i) a range of values that the patient status value may be in, and (ii) a probability that the patient status value may be in the range of values.

11. The method of claim 8, wherein the confidence interval for the patient status value is displayed graphically.

12. The method of claim 8, wherein a probability of the determined patient status value reaching a predetermined threshold is displayed.

* * * * *